(12) United States Patent
Rau et al.

(10) Patent No.: US 6,176,848 B1
(45) Date of Patent: Jan. 23, 2001

(54) INTRAVASCULAR BLOOD PUMP

(75) Inventors: Guenter Rau, Aachen; Helmut Reul, Dueren; Thorsten Siess, Aachen, all of (DE)

(73) Assignee: Impella Cardiotechnik GmbH, Aachen (DE)

( * ) Notice: Under 35 U.S.C. 154(b), the term of this patent shall be extended for 0 days.

(21) Appl. No.: 09/155,818

(22) PCT Filed: Apr. 2, 1997

(86) PCT No.: PCT/EP97/01661

§ 371 Date: Oct. 5, 1998

§ 102(e) Date: Oct. 5, 1998

(87) PCT Pub. No.: WO97/37698

PCT Pub. Date: Oct. 16, 1997

(30) Foreign Application Priority Data

Apr. 4, 1996 (DE) .............................. 196 13 564

(51) Int. Cl.[7] .............................. A61M 5/00; A61M 25/00
(52) U.S. Cl. .............................. 604/264; 623/3; 600/16; 600/17
(58) Field of Search .............................. 600/16–17; 604/93, 604/131, 151, 264; 623/1, 2, 3, 66; 417/420

(56) References Cited

U.S. PATENT DOCUMENTS

| | | |
|---|---|---|
| 3,568,659 | 3/1971 | Karnegis . |
| 4,382,199 | 5/1983 | Isaacson . |
| 4,625,712 | 12/1986 | Wampler . |
| 4,688,998 | 8/1997 | Olsen et al. . |
| 4,704,121 | 11/1987 | Moise . |
| 4,779,614 | 10/1988 | Moise . |
| 4,817,586 | 4/1989 | Wampler . |
| 4,846,152 | 7/1989 | Wampler et al. . |
| 4,895,557 | 1/1990 | Moise et al. . |
| 4,906,229 | 3/1990 | Wampler . |
| 4,908,012 | 3/1990 | Moise et al. . |
| 4,919,647 | 4/1990 | Nash . |
| 4,944,722 | 7/1990 | Carriker et al. . |
| 5,017,103 | * 5/1991 | Dahl ................................ 417/420 |
| 5,061,256 | 10/1991 | Wampler . |
| 5,092,879 | 3/1992 | Jarvik . |
| 5,112,292 | 5/1992 | Hwang et al. . |
| 5,376,114 | * 12/1994 | Jarvik ................................ 623/3 |
| 5,385,454 | 1/1995 | Kopbayashi et al. . |
| 5,385,581 | 1/1995 | Bramm et al. . |
| 5,393,207 | 2/1995 | Maher et al. . |
| 5,507,629 | 4/1996 | Jarvik . |
| 5,695,471 | * 12/1997 | Wampler ................................ 604/131 |
| 5,911,685 | 6/1999 | Siess et al. . |
| 5,921,913 | 7/1999 | Siess . |
| 5,964,694 | 10/1999 | Siess et al. . |

* cited by examiner

Primary Examiner—Mark O. Polutta
Assistant Examiner—Catherine Serke
(74) Attorney, Agent, or Firm—Fulwider Patton Lee & Utecht, LLP

(57) ABSTRACT

A blood pump having a motor housing and a pump housing which are rigidly connected to one another in an axially spaced relationship. Both housings are of substantially the same diameter and are sized to enable the pump to be introduced via catheter through the body's blood-vessel system. The impeller is mounted in the pump housing on a longitudinally and radially acting bearing designed as a point-support bearing. To avoid oscillation of the impeller, it is fitted with an alignment device which may have a hydrodynamic or mechanical action. Rotation of the motor is transferred to the impeller via a magnetic coupling.

8 Claims, 4 Drawing Sheets

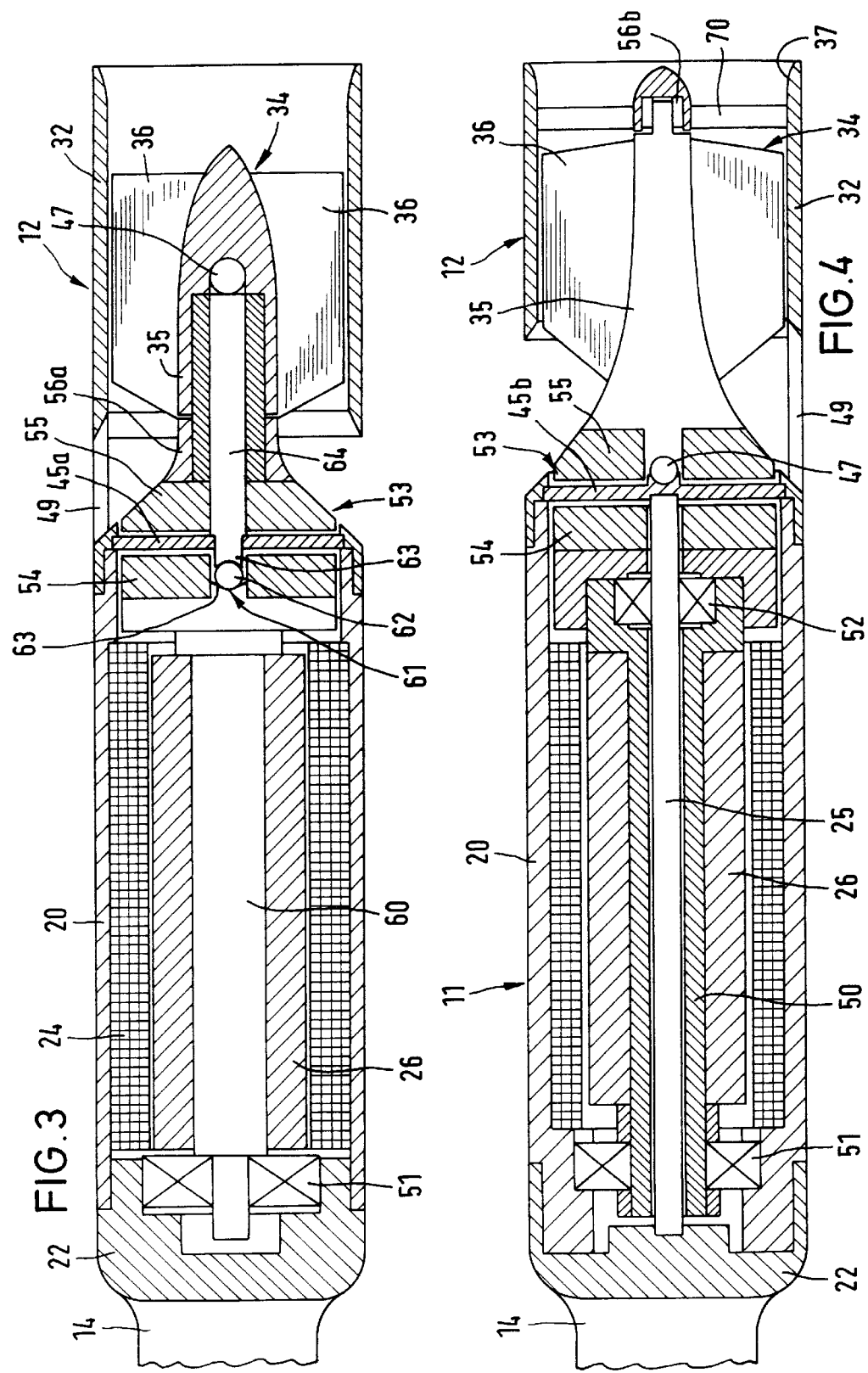

INTRAVASCULAR BLOOD PUMP

Figure 1:
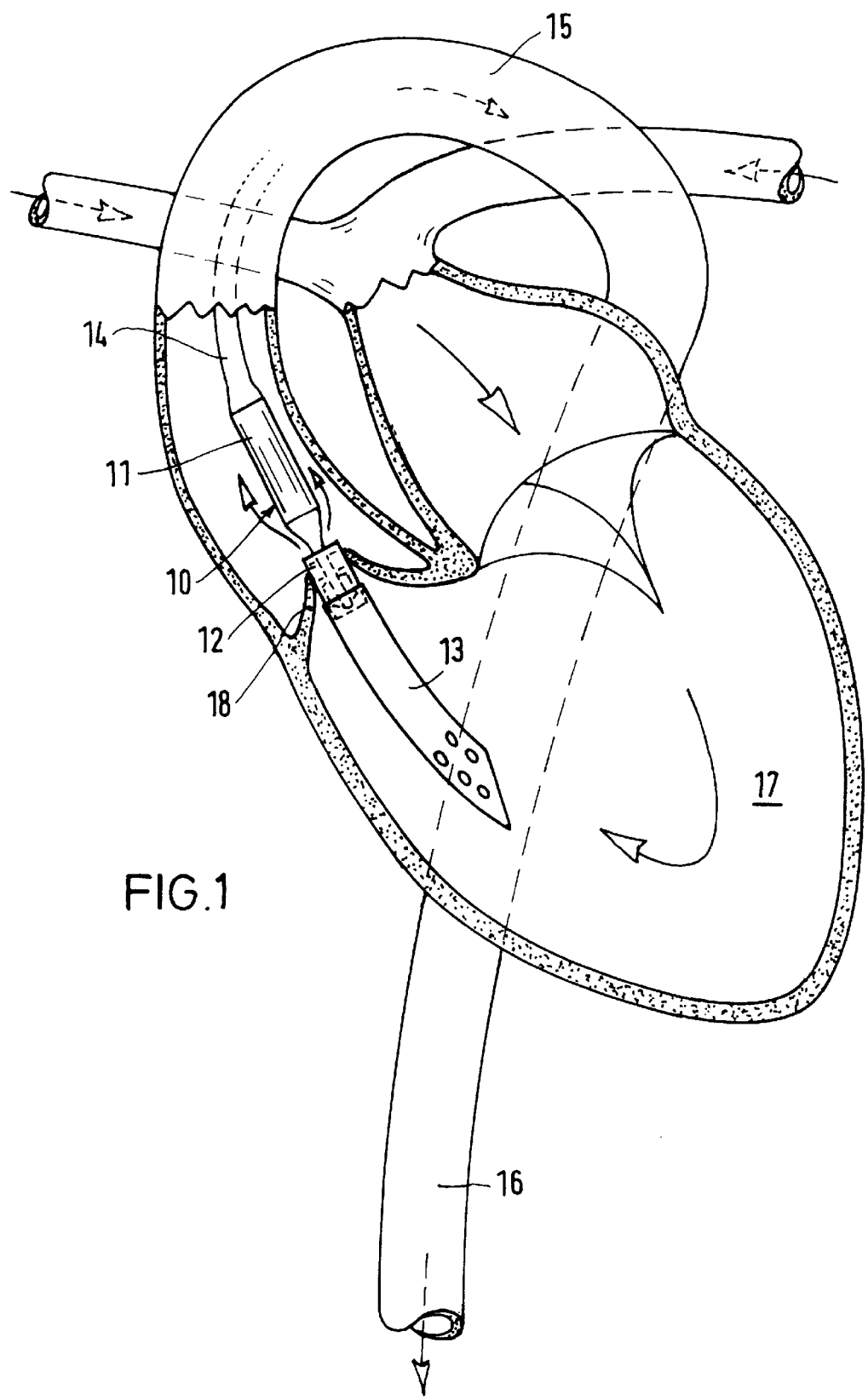

The invention relates to an intravascular blood pump comprising a drive unit and a pump unit, said blood pump being sized to be introduced through the vascular system of a human body to perform a pumping action, e.g., in the heart.

An intravascular blood pump is introduced through puncture of a blood vessel into the vascular system of the body and is advanced to the heart or to a different site where blood is to be pumped. Those parts which are inserted into the body must have a diameter small enough to allow them to fit through the externally accessible large vessels. The largest diameter permitted is about 7 mm.

From EP 0 157 871 B1 and EP 0 397 668 B1, intravascular blood pumps are known wherein the pump unit comprises a tubular housing having an impeller arranged for rotation therein. The impeller is connected to an extracorporeal drive unit via a flexible shaft guided through a catheter. The drive unit is arranged to drive the flexible shaft which in turn drives the pump unit. The drive unit, being operated at an extracorporeal site, can have any desired size. The desired reduction of the friction between the shaft and the catheter requires continuous lubrication by liquid. A part of this liquid containing abrasive particles will leak through the sliding bearing and the sealing of the pump unit and thus enter the blood stream. The remaining part will be collected extracorporeally after passing through the catheter along the shaft. Further, the flexible shaft restricts the range of applications of the blood pump because the latter can be advanced only to those sites in the body which do not require too extensive flexure of the catheter and the shaft accommodated therein.

A blood pump known from WO94/09835 is provided as a temporary supportive device for the heart. This blood pump, which is used on the surgically exposed heart, comprises a rod-shaped housing which contains the motor and the pump and can be inserted into the aorta by its pump portion whereas the motor portion remains external of the aorta.

Further, from EP 0 157 859 B1, there is known a blood pump wherein the motor unit and the pump unit are combined in one integral design. This pump is suited for implantation but is not useful as an intravascular blood pump to be introduced into the body by a minimum-invasion surgical intervention.

It is an object of the invention to provide an intravascular blood pump, i.e. a blood pump adapted to be advanced through blood vessels, which, while offering the required high pumping performance, is of small size and is sealed in a simple and safe manner.

It is a further object of the invention to provide an intravascular blood pump wherein the danger of hemotoxic damage due to shear stresses on the blood is largely reduced.

The blood pump according to the invention is defined by claim 1.

In the blood pump of the invention, the drive unit and the pump unit are directly connected to each other, and the blood pump is provided as a rod-shaped thin member, with the motor housing and the pump housing having the substantially the same outer diameter. The diameter of a blood pump to be positioned through a minimum-invasion intervention is restricted to about 5 to 7 mm since the width of vessels in the outer regions of the body is at maximum slightly above 7 mm. A blood pump of the instant type is suited to achieve a pumping performance of substantially 4 liters per minute at a counterpressure of about 100 mm Hg.

According to the invention, in an intravascular blood pump, the impeller is axially supported on a step bearing arranged external of the motor housing and is coupled to the motor shaft via a magnetic coupling through one end wall of the motor housing. Said end wall is an integral part of the motor housing and is provided to seal the same. This obviates the need to guide a rotating shaft through the motor housing. Thus, no sealings with a resultant danger of leakage or of blood depositing thereon will be required on this site. The end wall of the motor housing is made from a non-magnetic material, particularly of a synthetic material or ceramic. It is possible to support the impeller on a rod which is non-rotating and arranged to extend through the end wall of the motor housing. The sealing between the rod and the end wall poses no problems because both parts are stationary.

Further, according to the invention, orientation means are provided to hold the impeller in a coaxial orientation with the axis of the motor. First, the impeller is axially supported and radially centered relative to the housing by means of a step bearing. Still, such a step bearing which is arranged along the axis of the impeller cannot keep the impeller from performing oscillating movements around the step bearing. To restrict or preclude such oscillating movements, corresponding orientation means are provided which can be of a mechanical, magnetic or hydromechanical type and will cause the impeller to exactly maintain its axial orientation. The centered arrangement of the impeller relative to the pump housing is obtained by the step bearing. The radial orientation relative to the longitudinal axis is accomplished by the orientation means which are provided separately and at a distance from the step bearing.

Preferably, the rod supporting the impeller extends into the motor housing and thus obtains good guidance and constancy with regard to its axial orientation. This is of importance for a true, centrically precise guidance of the impeller. A guidance with such a high accuracy is necessary since, for minimizing hemotoxic damage and for avoiding hydraulic losses in efficiency, the gap between the blades of the impeller and the pump housing should not exceed a tenth of a millimeter. A faulty concentric running of the impeller would also increase the danger of hemolysis.

A further advantage of the blood pump resides in that the impeller can easily be dismounted and replaced. The motor housing and the pump housing form a unit onto which the impeller, provided as a separate and exchangeable part, is slipped until abutting on the step bearing. The unit comprising the drive unit and the pump housing is easily cleaned and disinfected since it does not include shaft passages or moving parts and is free of interspaces susceptible to contaminants depositing thereon.

Upon rotation of the impeller, the impeller conveys blood in the predetermined flow direction. In this situation, the impeller is subjected to a force which tends to pull the impeller away from the drive unit. The magnetic coupling by which the impeller is coupled to the motor shaft pulls the impeller against the step bearing, thus preventing that the impeller is pulled off from the step bearing during operation.

Because of its good mobility in the vascular system, the intravascular blood pump of the invention can be used in various applications, for instance a) as a left heart support pump with the option (cf. b)) to generate a pulsating flow, b) as a right heart support pump with the option of pulsatile operation by modulation of the pump speed, c) as a uni- or biventricular support system during thoracic/transthoracic surgical interventions on the beating or non-beating heart without using a heart-lung machine, d) as a blood pump provided for local perfusion of an organ and having a corresponding sealing device.

Embodiments of the invention will be explained in greater detail hereunder with reference to the drawings.

Figure 2:
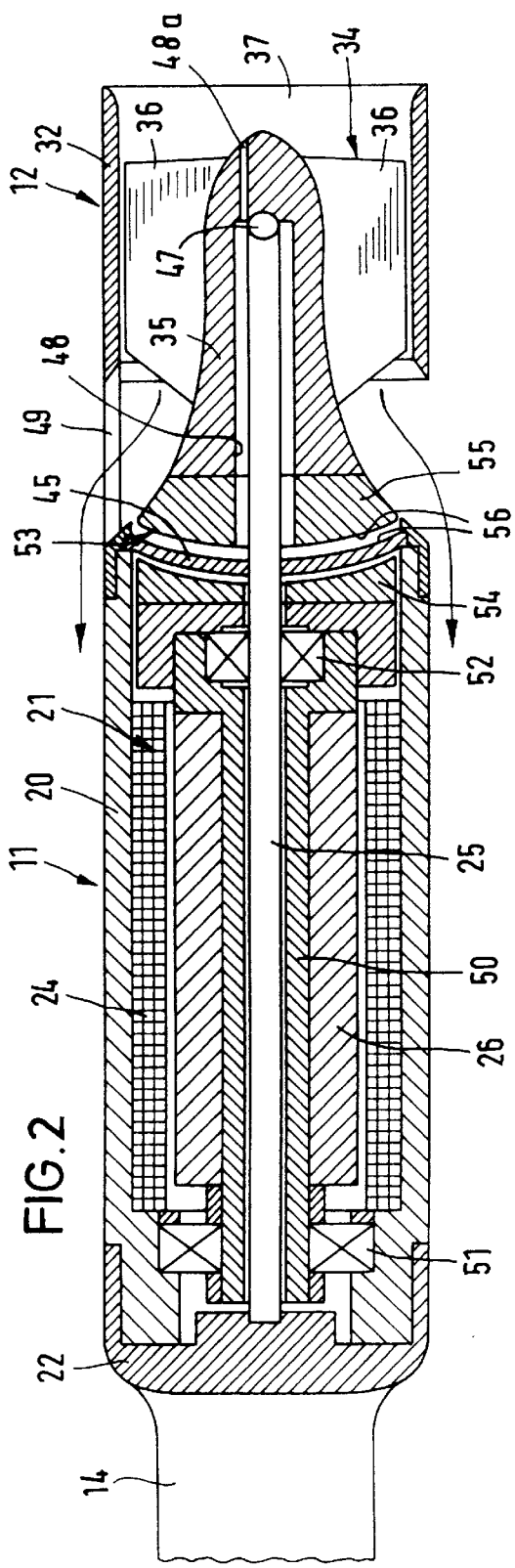
Figure 5:
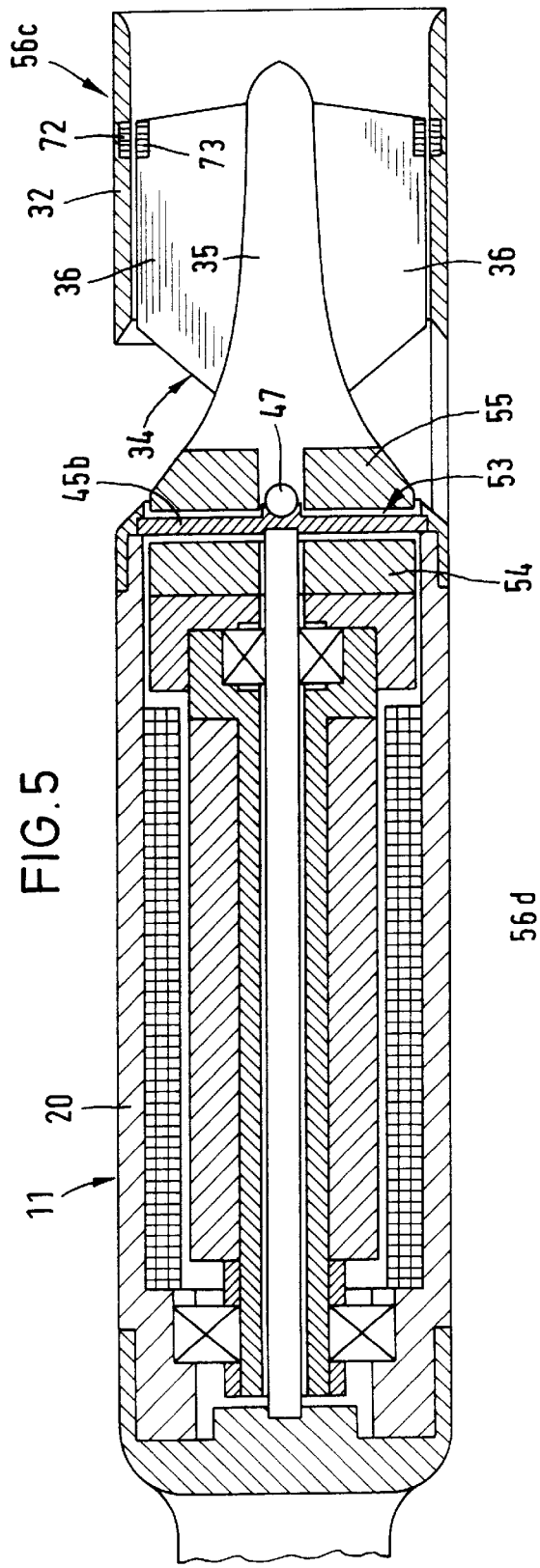
Figure 6:
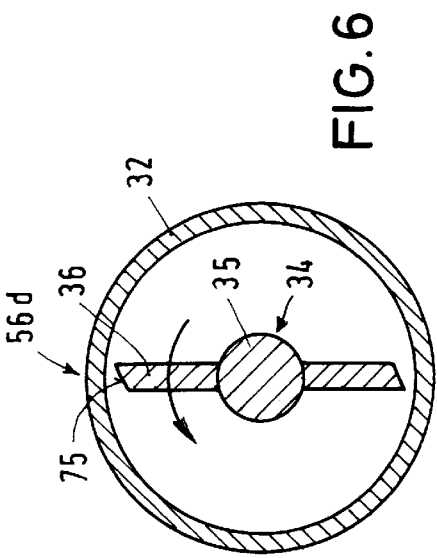

FIG. 1 is a systematic illustration of the insertion of the blood pump to a site before the left ventricle, with the suction cannula positioned inside the left ventricle, FIG. 2 is a systematic longitudinal sectional view of a first embodiment of the blood pump, FIG. 3 is a longitudinal sectional view of a second embodiment of the blood pump, FIG. 4 is a longitudinal sectional view of a third embodiment of the blood pump, FIG. 5 is a longitudinal sectional view of a forth embodiment of the blood pump, FIG. 6 is a front view of the impeller in a modified further embodiment.

FIG. 1 illustrates the use of the blood pump 10 for left ventricular cardio-active support. Blood pump 10 comprises a motor unit 11 and a pump unit 12 arranged coaxially in series and forming a rod-shaped design. The pump unit is extended by a suction hose 13 which on its end and/or in its side wall is provided with openings for blood supply to the pump. The rear end of blood pump 10 facing away from suction hose 13 is connected to a catheter 14 which has been introduced through the aortic arch 15 and the aorta 16. Blood pump 10 will be placed in a suitable manner to position it primarily in the ascending aorta while the straight and short suction hose 13 extends into the heart ventricle 17. The aortic valve will in the closed condition abut the outer side of the pump housing or the suction hose. The blood pump 10 along with the suction hose 13 arranged distally thereof is advanced to the illustrated position by advancing the catheter 14, optionally with a mandrel accommodated therein or by use of a guide wire. In the process, suction hose 13 passes the aortic valve 18 retrogradely so that blood will be sucked through suction hose 13 and be pumped into the aorta 16.

The use of the blood pump of the invention is not restricted to the application illustrated in FIG. 1 which merely shows a typical example.

FIG. 2 shows a preferred embodiment of the blood pump comprising the motor unit 11 and the pump unit 12 tightly connected thereto. Motor unit 11 has a longitudinal cylindrical housing 20 accommodating the electric motor 21. Housing 20 has its rear end closed by an end wall 22 joined by the flexible catheter 14 sealingly attached thereto. Guided through catheter 14 are, inter alia, the electric cables for power supply and control of the electric motor 21 passing therethrough.

The stator 24 of the motor comprises, in the usual manner, a plurality of circumferentially distributed coils as well as a magnetic return path in the longitudinal direction. The stator is tightly attached to motor housing 20. Stator 24 encloses a rotor 26 comprising permanent magnets magnetized in the radial direction. Rotor 26 is supported in motor housing 20 to be rotated therein.

The rotor 26 of the motor is mounted on a motor shaft 50 connected to rotor 20; motor shaft 50 is formed as a hollow shaft and has a rod 25 extending therethrough. Motor shaft 50 is connected on its rear end to a bearing 51 in the motor housing, and its front end is supported by a bearing 52 on rod 25.

Extending through motor housing 20 is a stationary, non-rotating rod 25 having its rear end connected to end wall 22. Rod 25 projects through an end wall 45 closing the front side of motor housing 20; within end wall 45, rod 25 is attached and provided with a stationary sealing. The front portion of rod 25 extends into the pump housing 32. This portion carries the hub 35 of impeller 34, with hub 35 being supported on the shaft end by a step bearing 47 of a spherical shape. Step bearing 47 is a combined axial/radial bearing. Formed in hub 35 is a bore 48 with oversize, with rod 25 extending therethrough with radial play so that hub 35 can perform slight oscillating movements around step bearing 47. Hub 35 is further formed with a scavenging bore 48a reaching from the front end of the hub to bore 48, thus effecting a steady flow through bore 48 to avoid thrombogenesis. Pump housing 32 is connected to motor housing 20 by longitudinal struts 49.

Hub 35 of impeller 34 is provided with blades 36 or pump buckets radially projecting therefrom. Upon rotation of impeller 34, blood is sucked through the suction opening 37 on the end side of pump housing 32 and is driven to the rear in the axial direction within pump housing 32. Through the annular gap between pump housing 32 and motor housing 20, the blood will flow to the outside along the hub 35 which is widening in the flow direction, and will then continue its flow along motor housing 20. This provides for dissipation of the heat generated in the drive unit without causing hemotoxic damage due to excessive surface temperatures (above 41° C.) on motor housing 20. Motor housing 20 and pump housing 32 are substantially equal in diameter, although the outer diameter of pump housing 32 can be slightly larger than that of the motor housing because the pump housing does not need to be surrounded by a flow. Pump housing 32 comprises a cylindrical tube with open front and rear ends. In the present and the following examples, it is also possible to operate the pump unit in the reverse conveying direction, with blood being sucked along the motor housing and issuing axially out of end 37.

The rotation of motor shaft 50 is transmitted to impeller 34 through a magnetic coupling 53. The magnetic coupling comprises first magnetic portions 54 arranged within the motor housing and connected to motor shaft 50, and second magnetic portions 55 connected to hub 35. The two magnetic portions are coupled to each other through the non-magnetic end wall 45. The magnetic holding force of coupling 53 is strong enough to overcome that force which during operation of the pump tends to drive the impeller 34 in the forward direction (to the right side in FIG. 4) so that the impeller 34 with the hub 35 is kept in position on rod 25 exclusively by a the magnetic holding force.

The end wall 45, as well as the adjacent walls of the magnetic portions 54 and 55, is curved in a concave shape towards the interior of the motor housing, with the step bearing 47 forming the center of the curvature. This curvature and the magnetic portions of the coupling arranged flush in the axial direction, are effective, together with the holding force of the magnetic coupling 53, to lend radial stability by means of liquid damping to the hub which is supported in the manner of a pendulum on step bearing 47. The curvatures of end wall 45 and of the adjacent wall of impeller 34 constitute an orientation means 56 to hold the impeller in a coaxial orientation relative to rod 25 during the pumping operation.

In the embodiment according to FIG. 3, the end of motor housing 20 facing towards impeller 34 is closed by a plane end wall 45a. Rotor 26 is mounted to a rotor shaft 60 having its rear end supported on a ball bearing 51 and having its front end supported on a bearing 61. Bearing 61 comprises a ball 62 arranged along the axis of rotor shaft 60 while seated in a conical emplacement 63 of the rotor shaft and forming a conical bearing on which the rotor shaft is axially supported. Ball 62 is further seated in a bearing recess formed in a shoulder 63 projecting from end wall 45a into the interior of the housing. Motor housing 20 is tightly encapsulated all around. For transmission of the rotation of rotor shaft 60 to the impeller 34, a magnetic coupling 53 is provided, comprising first magnetic portions 54 arranged within motor housing 20 and connected to rotor shaft 60, and second magnetic portions 55 connected to impeller 34. The first magnetic portions 54 and the second magnetic portions 55 attract each other through end wall 45a. Thus, when the rotor shaft 60 is rotated, impeller 34 is rotated along with it.

A rod 64, projecting outwards from end wall 45a, extends into hub 35 of impeller 34 and has its end abutting a ball forming the step bearing 47 and attached within hub 35. To stabilize the orientation of hub 35, there is provided an orientation means 56a formed as a sliding bearing attached within hub 35 for rotation about rod 64. Step bearing 47 lends axial support to impeller 34. The orientation means 56a formed as a sliding bearing for its part effects a highly exact radial centering and prevents oscillation of the impeller around step bearing 47 and maintains the impeller in a coaxial orientation with the axis of the motor. The ball of step bearing 47 is preferably made from ceramics or another wear-resistant material. Said ball is arranged for common rotation with the impeller.

In the blood pump according to FIG. 4, the motor is generally designed in the same manner as shown in FIG. 2. Extending through the hollow motor shaft 50 is a rod 25 which is centered and attached in the rear end wall 22 and the front end wall 45b. Motor shaft 50 is supported on its rear end by a bearing 51 in motor housing 20, and has its front end supported by a bearing 52 on rod 25. Motor shaft 50 has attached thereon the first magnets 54 of a magnetic coupling 53. The second magnets 55 of the magnetic coupling are attached to hub 35 of impeller 34.

Step bearing 47 comprises a ball arranged centrically between the second magnets 55 and supported on end wall 45b of motor housing 20. In contrast to the preceding embodiments, the step bearing 47 of FIG. 4 is arranged on the motor-side end of impeller 34, avoiding the need for a long support arm projecting from end wall 45b.

According to FIG. 4, the orientation means comprises a bearing 56b supporting the upstream end of hub 35 of impeller 34 in pump housing 32. For this purpose, a spider 70 is provided in pump housing 32 near intake opening 37 for holding the orientation means 56b. Thus, impeller 34 is mechanically supported on both of its ends.

In the embodiment according to FIG. 5, drive unit 11 is designed in the same manner as in FIG. 4. Also step bearing 47 is arranged in the same manner near end wall 45b of motor housing 20. A difference resides in the orientation means 56c. The orientation means 56c of FIG. 5 comprises magnets 72,73 of which the magnets 72 are arranged in the wall of pump housing 32 and the magnets 73 are arranged in the blades 36 of impeller 34. The magnets are arranged to have their like polarities face towards each other and repel each other. In this manner, impeller 34 is held centered within the pump housing.

FIG. 6 shows another embodiment of the orientation means 56d. The orientation means here comprises inclined portions 75 provided on the outer ends of the blades 36 of impeller 34, with the distance between blade 36 and the surrounding wall of pump housing 32 decreasing in the direction opposite to the direction of rotation. This means that a pressure buildup will be generated between the inclined face 75 and the surrounding wall of pump housing 32, acting in a radially inward direction on blade 36. This feature provides for a hydrodynamic centering of impeller 34.

What is claimed is:

1. An intravascular blood pump connected to a catheter, comprising:

a motor housing having an electric motor with an output shaft disposed therein, said motor housing having an end wall;

a tubular pump housing coaxially arranged with said motor housing and axially spaced therefrom, said tubular pump housing having a diameter substantially the same as said motor housing;

a suction opening formed on the end of said tubular pump housing facing away from said motor housing;

an impeller rotationally disposed in said tubular pump housing;

a magnetic coupling for transferring rotation of said output shaft to said impeller through said end wall;

a step bearing arranged externally to said motor housing for axially supporting said impeller; and an orientation means for maintaining said impeller in a coaxial orientation with the axis of said pump housing.

2. The blood pump according to claim 1, wherein said impeller has a bore formed therein and further comprising a rod that projects from said end wall of said motor housing into said bore to support said step bearing.

3. The blood pump of claim 2, wherein said orientation means comprises a radial bearing for supporting said impeller on said rod.

4. The blood pump of claim 2, wherein said orientation means comprises a concave configuration of said end wall of said motor housing and a convex configuration of an end of said impeller adjacent thereto such that liquid flowing along said impeller in combination with force generated by said magnetic coupling is effective for centering said impeller when oscillating about said step bearing.

5. The blood pump according to claim 1, wherein said orientation means comprises a concave configuration of said end wall of said motor housing and a convex configuration of an end of said impeller adjacent thereto such that liquid flowing along said impeller in combination with force generated by said magnetic coupling is effective for centering said impeller when oscillating about said step bearing.

6. The blood pump of claim 1, wherein said impeller includes blades and extends away from said motor housing beyond said blades and wherein said orientation means comprises a radial bearing attached to said motor housing for supporting said impeller at a point beyond said blades.

7. The blood pump of claim 1, wherein said impeller includes blades and said orientation means comprises a first set of magnets disposed in said blades and a counterpart second set of magnets disposed in said pump housing.

8. The blood pump of claim 1, wherein said impeller includes blades and said orientation means comprises a configuration in the ends of such blades to provide for hydrodynamic centering of said impeller during rotation of said impeller in said pump housing.

* * * * *